(12) United States Patent
Nadaoka et al.

(10) Patent No.: US 7,575,915 B2
(45) Date of Patent: *Aug. 18, 2009

(54) BIOSENSOR

(75) Inventors: Masataka Nadaoka, Iyo (JP); Mie Takahashi, Niihama (JP); Hirotaka Tanaka, Matsuyama (JP); Fumihisa Kitawaki, Kadoma (JP)

(73) Assignee: Panasonic Corporation, Osaka (JP)

( * ) Notice: Subject to any disclaimer, the term of this patent is extended or adjusted under 35 U.S.C. 154(b) by 557 days.

This patent is subject to a terminal disclaimer.

(21) Appl. No.: 10/031,988

(22) PCT Filed: May 25, 2001

(86) PCT No.: PCT/JP01/04419

§ 371 (c)(1),
(2), (4) Date: May 6, 2002

(87) PCT Pub. No.: WO01/90754

PCT Pub. Date: Nov. 29, 2001

(65) Prior Publication Data

US 2002/0137230 A1    Sep. 26, 2002

(51) Int. Cl.
*G01N 33/558* (2006.01)

(52) U.S. Cl. .................. 435/287.2; 422/56; 422/58; 435/287.1; 435/287.7; 435/287.8; 435/287.9; 435/810; 435/970; 436/514; 436/518; 436/169; 436/805; 436/807

(58) Field of Classification Search .................. 435/7.1, 435/180–182, 287.1–287.2, 287.7, 287.8, 435/805, 970–971; 436/514, 518, 522, 535, 436/169–170, 810; 422/56–57, 61, 68.1, 422/255

See application file for complete search history.

(56) References Cited

U.S. PATENT DOCUMENTS

| | | | | |
|---|---|---|---|---|
| 3,715,192 A | * | 2/1973 | Wenz et al. | 422/56 |
| 4,252,538 A | * | 2/1981 | Barr | 435/7.25 |
| 4,883,764 A | * | 11/1989 | Kloepfer | 436/63 |
| 5,166,051 A | * | 11/1992 | Killeen et al. | 435/7.1 |
| 5,234,813 A | * | 8/1993 | McGeehan et al. | 435/7.9 |
| 5,416,000 A | * | 5/1995 | Allen et al. | 435/7.92 |
| 5,602,040 A | | 2/1997 | May et al. | |

(Continued)

FOREIGN PATENT DOCUMENTS

EP        0291194 B1    11/1988

(Continued)

*Primary Examiner*—Christopher L Chin
(74) *Attorney, Agent, or Firm*—Wenderoth, Lind & Ponack, L.L.P.

(57) ABSTRACT

A biosensor is provided with a development layer for developing an inspection target solution, that has a reagent immobilization part where an antibody for a measurement target in the inspection target solution is immobilized and a reagent holding part which marks in a dry state and holds an antibody which can be eluted by development of the inspection target solution in parts of the development layer. The biosensor measures a bonding amount of the marker reagent bonded to the reagent immobilization part, thereby qualitatively or quantitatively measuring components to be measured in the inspection target solution, and is further provided with a space forming material that forms a cavity part, which is a space into which the inspection target solution flows, between the development layer for developing the inspection target solution and the space forming material.

32 Claims, 7 Drawing Sheets

U.S. PATENT DOCUMENTS

| | | | |
|---|---|---|---|
| 5,607,863 A | | 3/1997 | Chandler |
| 5,824,268 A | * | 10/1998 | Bernstein et al. ............... 422/56 |
| 5,939,331 A | * | 8/1999 | Burd et al. .................. 436/518 |
| 5,985,675 A | * | 11/1999 | Charm et al. ............... 436/514 |
| 6,124,138 A | * | 9/2000 | Woudenberg et al. ....... 436/518 |
| 6,194,224 B1 | * | 2/2001 | Good et al. ................. 436/518 |

FOREIGN PATENT DOCUMENTS

| | | |
|---|---|---|
| EP | 0 447 154 | 9/1991 |
| EP | 0 903 584 | 3/1999 |
| EP | 1 003 038 | 5/2000 |
| EP | 1 143 247 | 10/2001 |
| EP | 1 186 889 | 3/2002 |
| JP | 8-285849 | 11/1996 |
| JP | 9-506434 | 6/1997 |
| JP | 9-178748 | 7/1997 |
| JP | 10-274624 | 10/1998 |
| JP | 10-274653 | 10/1998 |

* cited by examiner

BIOSENSOR

TECHNICAL FIELD

The present invention relates to a biosensor and, more particularly, to a biosensor utilizing a chromatography.

BACKGROUND ART

A conventional biosensor is provided with a development layer for developing an inspection target solution, a reagent immobilization part immobilized on a part of the development layer and a reagent holding part where a marker reagent which can be eluted by development of the inspection target solution is held, wherein a bonding amount of the marker reagent in the reagent immobilization part is measured, thereby qualitatively or quantitatively measuring components to be measured in the inspection target solution. An example of such a biosensor is an immuno-chromatographic sensor.

The immuno-chromatographic sensor is generally constituted by an application layer where an inspection target solution is applied, plural development layers, and a water absorbing layer at the end of the development layers. These development layers have an antibody immobilization part where an antibody for components to be measured in the inspection target solution is immobilized in a part thereof, and a marked antibody is held in a marker reagent holding part on the application layer side with respect to the antibody immobilization part, in a dry state where the marked antibody can be eluted by the inspection target solution.

In this immuno-chromatographic sensor, a required amount of inspection target solution is applied to the application layer and the inspection target solution permeates porous materials provided on the development layers, thereby starting the measurement.

As methods for applying the inspection target solution, there have been employed a method for soaking an application part in the inspection target solution for a definite period of time, a method for applying a predetermined amount of inspection target solution employing a high-precision dispenser, a dropper, or the like, a method for directly applying the inspection target solution to the application part for a definite period of time at urination when urine or the like is taken as the inspection target solution, or the like.

A measurement result of the immuno-chromatographic sensor is detected by a marked antibody bonded to the antibody immobilization part. With respect to this marked antibody, a typical marker is gold colloid particles, by which the bonding in the antibody immobilization part can be seen, and the measurement result can be obtained visually. While a sandwich reaction of an antigen antibody reaction by which a complex of an immobilized antibody, a measurement target, and the marked antibody is formed is taken as a measurement principle here, the measurement result can also be obtained by confirming a bonding state of the marker reagent in the antibody immobilization part or an antigen immobilization part even when other competitive reactions are similarly taken as measurement principles.

Further, while a visual qualitative judgement is required with respect to the measurement result by the above-mentioned sandwich reaction, in a case where a semi-quantitative or more accurate judgement is required for a required measurement result, there are also a method for reading by a transparent mode employing an optical reading device, which is disclosed in Japanese Published Patent Application No. Hei. 10-274624, and a method for taking-in a measurement result as an image by a camera or the like to be processed arithmetically, which is disclosed in Japanese Published Patent Application No. Hei. 10-274653.

In recent years, a quick, simple, and accurate measuring device which is easily available at a low cost has been desired with a concept of POC (Point of Care) in the medical and diagnostic scene. However, according to the above-described conventional methods, when the inspection target solution, which is blood for example, is applied to a sensor part, it has been required that blood is collected employing an injector, generally subjected to an operation for separating blood corpuscles as concrete components and blood plasma employing a centrifugal separator, and applied to the sensor part employing a tool such as a dispenser or a dropper.

This method for collecting blood by an injector requires special skills in medical technology, and the necessity of the centrifugation operation makes it impossible to perform self-measurements in a household or by individuals not having the ability to perform centrifugation process.

Further, since the tool such as a dispenser is required for quantitatively measuring the inspection target solution, the operation becomes complicated.

Further, when the inspection target solution is urine or the like, there is a method in which urine is collected in a container such as a paper cup once and a part of the sensor is soaked therein for a definite period of time, a method in which collected urine is applied employing a dispenser, dropper, or the like as in the case of blood, when a predetermined volume of inspection target solution is required to be quantitatively measured, and a method in which urine is directly applied to an application part for a definite period of time at urination in the case of a relatively low-accuracy sensor which does not require quantitative accuracy in a measurement. In these methods, however, urine is required to be collected in a paper cup or the like once, or there is no means for accurately defining the volume of the inspection target solution in a case where urine is directly applied, resulting in restriction to a qualitative measurement with low accuracy and the like.

The present invention is made to solve the above-mentioned problems and has for its object to provide a biosensor which requires no sophisticated device or operation and can perform a simple and high-accuracy measurement even with a small volume of inspection target solution.

SUMMARY OF THE INVENTION

According to the present invention, there is provided a biosensor which includes, in parts of a development layer for developing the inspection target solution, a reagent immobilization part immobilized therein and a marker reagent holding part where a marker reagent which can be eluted by development of an inspection target solution is held, wherein the biosensor measures a bonding amount of the marker reagent in the reagent immobilization part, thereby qualitatively or quantitatively measuring components to be measured in the inspection target solution. The biosensor further includes a space forming part which forms a cavity part that is a space into which the inspection target solution flows, between the development layer and the space forming part. Therefore, there is no need to use a high-accuracy dispenser or the like when the inspection target solution is applied to the cavity part, and, even when a small and unknown amount of inspection target solution is dropped, the drop is brought into contact with the cavity part, so that the inspection target solution is surely absorbed into the cavity part, resulting in a simple and high-accuracy measurement.

According to the present invention, there is provided a biosensor which includes a reagent immobilization part immobilized in a part of a development layer for developing the inspection target solution, and measures a bonding amount of the marker reagent in the reagent immobilization part, thereby qualitatively or quantitatively measuring components to be measured in the inspection target solution, and this biosensor further includes: a space forming part which forms a cavity part that is a space into which the inspection target solution flows, between the development layer and the space forming part; and a marker reagent holding part for holding a marker reagent which can be eluted by flowing-in of the inspection target solution, in the cavity part. Therefore, the marker reagent in the inspection target solution in the cavity part is dissolved and diffused when the inspection target solution is introduced in the cavity part, whereby the marker reagent can be diffused more uniformly with respect to the inspection target solution, resulting in a simple and high-accuracy measurement.

According to the present invention, in the biosensor, the cavity part temporarily holds the inspection target solution. Therefore, the amount of aspirating the inspection target solution permeating the cavity part can be confirmed and more accurate permeation in the development layer is possible, thereby implementing a higher-accuracy measurement with a reduced erroneous measurement operation and specimen shortage.

According to the present invention, in the biosensor, the cavity part defines the amount of the flowing-in of the inspection target solution by the volume of the cavity part. Therefore, neither an operation of quantitatively measuring a predetermined volume of inspection target solution in advance nor special skills for specimen collection or the like is required, thereby implementing a measurement with a simple operation.

According to the present invention, in the biosensor, the cavity part has a volume for the flowing-in of the inspection target solution enough to develop in the development layer. Therefore, the space has enough volume for the amount of inspection target solution required for a measurement, so that specimen shortages are solved, resulting in a higher-accuracy measurement.

According to the present invention, the biosensor further includes a cell component destruction reagent part for destroying cell components in the cavity part. Therefore, in a measurement employing the inspection target solution which includes cell components such as blood, the inspection target solution can be applied to the cavity part directly without previously performing an operation of centrifugation or the like, and the applied inspection target solution is aspirated to the cavity part, thereby requiring no application device nor device for preprocessing the inspection target solution, when the inspection target solution is applied, resulting in a measurement with a simple operation.

According to the present invention, the biosensor further includes a cell component shrinkage reagent part for shrinking cell components in the cavity part. Therefore, even when the inspection target solution having cell components is employed, the development layer is not clogged with the cell components due to an action of a cell component shrinker, thereby easily performing a measurement operation as well as obtaining a high-accuracy result.

According to the present invention, the biosensor further includes a bleaching reagent part in the cavity part. Therefore, an adverse effect on a measurement, which is due to a color having no relation to the reaction, such as a color of the inspection target solution, remaining in the reagent immobilization part where the reaction is read, is reduced, thereby obtaining a high-accuracy measurement result.

According to the present invention, in the biosensor, the cavity part has a volume of 20 µl (microliter) or less. Therefore, even when the inspection target solution is small in amount or a small and unknown amount of inspection target solution which is collected with a blood collecting puncture device is measured, the inspection target solution is applied to the cavity part of defined volume, thereby introducing an accurate volume of inspection target solution, resulting in a high-accuracy measurement even with a small amount of inspection target solution.

According to the present invention, in the biosensor, the cavity part has a means for externally checking on flowing-in of the inspection target solution. Therefore, flowing-in of the inspection target solution in the measurement is checked on or detected, thereby to detect a measurement start time, and an appropriate amount of inspection target solution is obtained, thereby to solve specimen shortages and detect an accurate measurement start time, resulting in a higher-accuracy measurement.

According to the present invention, in the biosensor, the space forming part is partially or entirely light permeable. Therefore, the amount of aspirating the inspection target solution can be observed visually or employing an optical measurement method from the outside, thereby eliminating an erroneous measurement operation due to shortage in the amount of inspection target solution, resulting in a higher-accuracy measurement.

According to the present invention, the biosensor further includes a separation part for separating concrete components unnecessary for a measurement in the cavity part. Therefore, concrete components in the inspection target solution which are unnecessary for a measurement can be separated, and there is no need to previously eliminate the concrete components in the inspection target solution which are unnecessary for the measurement by an operation of centrifugation, filtration, or the like, resulting in a simple and high-accuracy measurement.

According to the present invention, the biosensor further includes a specimen holding part for holding the inspection target solution so as to be in contact with the cavity part. Therefore, an operation for moving the inspection target solution to another container after collecting the inspection target solution or an operation for quantitatively measuring a predetermined volume of collected inspection target solution is not required, and the inspection target solution can be held in the specimen holding part, thereby reducing outside pollution by the specimen, resulting in a safe, sanitary, quick, and simple measurement with high accuracy.

According to the present invention, in the biosensor, the specimen holding part holds a larger amount of inspection target solution than the volume of the cavity part. Therefore, sufficient volume of inspection target solution required for a measurement can be held, scattering of the inspection target solution to the outside and pollution thereby can be prevented, which results in a safe and sanitary measurement, and shortage of the inspection target solution can be solved, which results in an accurate measurement.

According to the present invention, in the biosensor, the bottom surface of the specimen holding part is as high as or higher than that of the cavity part 1. Therefore, the inspection target solution easily flows into the cavity part, resulting in an accurate measurement.

According to the present invention, in the biosensor, the cavity part has a volume of 100 µl or less. Therefore, a small amount of inspection target solution can be aspirated, and a measurement operation is easily performed to keep the operationality high.

According to the present invention, the biosensor further includes an air vent for assisting the flowing-in of the inspection target solution in the cavity part. Therefore, air in the cavity part which exists before the specimen is flowed in comes out surely, whereby the inspection target solution can be flowed in the cavity part quickly and surely.

According to the present invention, the biosensor further includes a porous material which can be permeated by permeation of the inspection target solution in the cavity part. Therefore, when the inspection target solution flows in the cavity part, a porous material serves as a subsidiary material for the flowing-in to ease the same, and impurities in the inspection target solution are trapped by the porous material, thereby reducing inhibition of flowing-in and permeation in the development layer.

According to the present invention, in the biosensor, whole reagents including the reagent in the reagent immobilization part and the marker reagent are in a dry state and they are entirely in a dry state. Therefore, a biosensor which is excellent in storage stability and is freely portable can be obtained.

According to the present invention, in the biosensor, the biosensor is employed for an immuno-chromatography. Therefore, in the immuno-chromatography which is utilized as a simplified method, there is no need to quantitatively measure a predetermined volume of inspection target solution with a high-accuracy dispenser or the like, and a predetermined volume of inspection target solution can be quantitatively measured accurately by the cavity part with an indefinite amount of inspection target solution being applied, thereby realizing a higher-accuracy measurement.

According to the present invention, in the biosensor, the biosensor is employed for a one-step immuno-chromatography. Therefore, in the one-step immuno-chromatography which is utilized as a simplified immunoassay method, a user does not have to quantitatively measure the volume of the inspection target solution previously at measurement, and an erroneous judgement due to mismeasurement of the amount of the solution is reduced, thereby realizing a more accurate measurement without failing of a simplified operation of a conventional one-step immuno-chromatography.

DETAILED DESCRIPTION OF THE INVENTION

Embodiment 1

Figure 1:
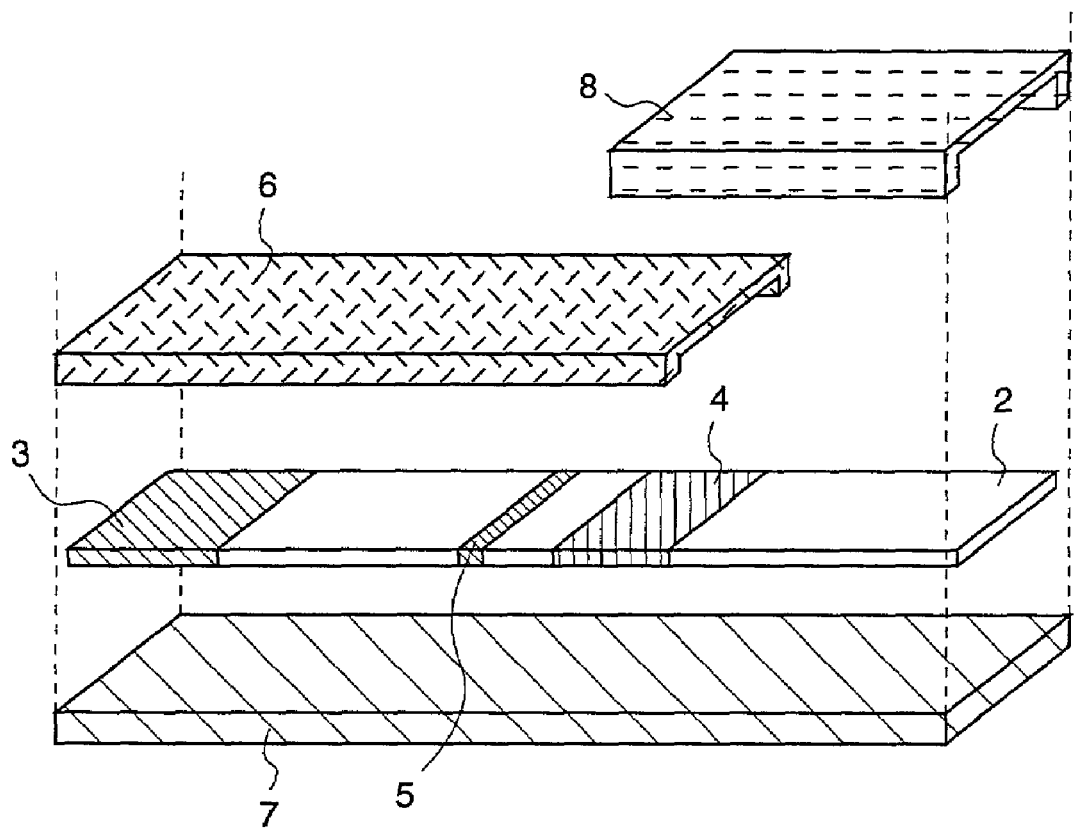
FIGS. 1(a) and 1(b) are structural diagrams of a biosensor according to a first embodiment of the present invention.
Figure 1:
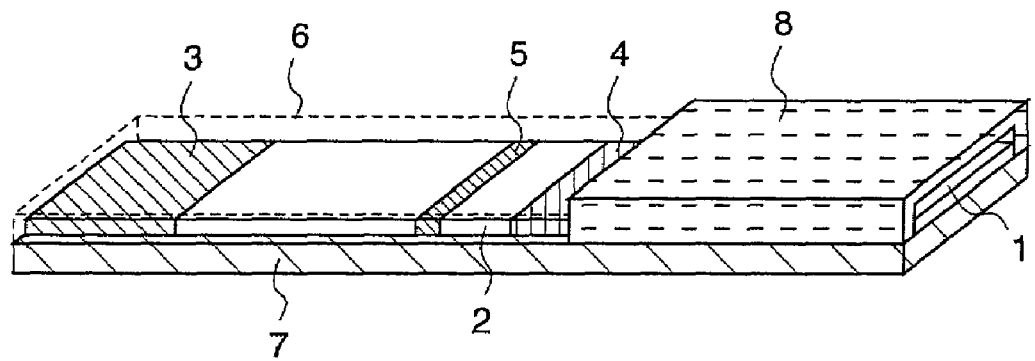

FIGS. 1(a) and 1(b) are examples of structural drawings of a biosensor according to a first embodiment of the present invention; where FIG. 1(a) is an exploded view of the biosensor and FIG. 1(b) is a perspective view of the biosensor.

In FIGS. 1(a) and 1(b), numeral 2 denotes a development layer for developing an inspection target solution, and is composed of cellulose nitrate. Numeral 3 denotes a water absorbing layer in the development layer 2, and is composed of glass fiber filter paper. As a material used for the development layer 2, any arbitrary porous material, such as filter paper, a nonwoven fabric, a membrane, and a cloth, which can be penetrated by the inspection target solution, are available. Further, the inspection target solution and a specimen are actually the same in this specification.

Numeral 4 denotes a marker reagent holding part in a part of the development layer 2, where an antibody for a measurement target in the inspection target solution is held, being marked with a gold colloid, in a dry state where the antibody can be eluted by the development of the inspection target solution. Numeral 5 denotes a reagent immobilization part in a part of the development layer 2, where the antibody for the measurement target in the inspection target solution is immobilized, and the antibody for the measurement target in the inspection target solution is bonded with the measurement target with an epitope different from that of the marker reagent held in the marker reagent holding part 4 and immobilized in a dry state so as to form a complex with the measurement target in the inspection target solution.

Further, the gold colloid which marks the antibody in the marker reagent holding part 4 is selected as a means for detecting the bonding in this reagent immobilization part 5, and others such as an enzyme, a protein, coloring matters, a fluorescene, and coloring particles such as a latex can be selected arbitrarily.

Numeral 6 denotes a liquid-impermeable sheet material which adherently covers the development layer 2 except a part thereof, and is composed of transparent PET tape here. Further, the development layer 2 is covered with this liquid-impermeable sheet material 6, whereby it is possible to protectingly intercept applying of the inspection target solution to a part other than the application part as well as to prevent external pollution by improvidently touching the inspection target solution or an inspector directly touching the development layer 2 with his/her hand or the like. Since the liquid-impermeable sheet material 6 covering the reagent immobilization part 5 is a part for confirming a measurement result, it is preferably formed of a transparent material, at least, to have a state where the inspection target solution is permeable. In a case where a high-accuracy measurement is required, it may also be possible to seal not only the top of the development layer 2 covered with the liquid-impermeable sheet material 6 but also its side faces parallel to the direction of the inspection target solution permeating.

Numeral 7 denotes a base material holding the development layer 2, and is composed of a white PET film. This base material 7 plays a role of reinforcing the development layer 2, and when a solution which poses a risk of infection, such as blood, saliva, and urine, is employed as the inspection target solution, the base material 7 also has effects of intercepting it.

Further, it is also possible that the base material 7 has effects of intercepting light in a case where the permeated development layer 2 becomes light permeable.

Numeral 8 denotes a space forming material for forming a cavity part 1 that is space through which the inspection target solution flows into the development layer 2 by a capillary phenomenon, and is constituted by laminating transparent PET films. This space forming material 8 also plays a role of protecting from pollution by the improvident inspection target solution being attached or scattering to the outside, when a biosensor to which the inspection target solution has been applied is handled.

Further, the space forming material 8 may be provided with an air vent for assisting the flowing-in of the inspection target solution in the cavity part 1. According to the shape of the air forming material 8, ends of the cavity part 1 other than the end to which the inspection target solution is attached may be blocked with side walls, and in this case, even when a specimen is attached to the opened end of the cavity part 1, air existing in the cavity part 1 does not or hardly comes out of the cavity part 1 before the specimen is introduced, whereby the introduction of the inspection target solution to the cavity part 11 is delayed or the introduction is not performed at all, resulting in a low-accuracy measurement result or an erroneous measurement result. On the other hand, when the air vent is provided in the space forming material 8, air in the cavity part 1 can come out and the specimen easily flows in the cavity part 1, thereby preventing occurrence of an adverse effect on the measurement. While this air vent is preferred to be provided at a backmost part of the cavity part, seen from the direction of the inspection target solution flowing-in, it may be provided at parts other than the backmost part according to need. As a material of the space forming material 8, a synthetic resin material such as ABS, polystyrene, and polyvinyl chloride, as well as a solution-impermeable material such as metal and glass can be employed, and, while the material is preferably transparent or translucent to check on the flowing-in of the inspection target solution into the cavity part 1, if not transparent, a colored or opaque material is also available.

The cavity part 1 is formed by arranging the space forming material 8 on the development layer 2, wherein the cavity part 1 is adjacent to the development layer 2, so that the inspection target solution flows in the cavity part 1 and starts permeating the development layer 2, thereby performing a measurement. To perform a high-accuracy measurement when the inspection target solution is small in amount or a small and unknown amount of inspection target solution which is collected with a blood collecting puncture device is measured, the cavity part 1 preferably has a volume of 20 µl (microliter) or less.

In a case where the inspection target solution having cell components is taken as a specimen, a cell shrinkage reagent is preferably held in the cavity part 1, and potassium chloride is employed as the cell concentration reagent, for example. By providing this cell shrinkage reagent, even when the inspection target solution having cell components is employed, a measurement operation can be performed easily without quantitatively measuring a predetermined volume of inspection target solution employing a high-accuracy dispenser or the like, and a high-accuracy measurement result can be obtained without clogging the development layer with the cell components due to an action of a cell component shrinker. The cell shrinkage reagent is a reagent provided when the cell components are included in the inspection target solution, and is not particularly required when the inspection target solution including no cell components is employed. Further, the cell component shrinker may be an inorganic compound including salt, such as inorganic salt other than the potassium chloride, natrium chloride, or sodium phosphate, amino acid such as glycine or glutamic acid, imino acid such as proline, sugars such as glucose, sucrose, or trehalose, and sugar alcohol such as glucitol in the same way, as long as they have effects of shrinking cells. A system including such a cell component shrinker is particularly effective when whole blood is employed as the inspection target solution.

Further, sodium percarbonate can also be held in the cavity part 1 as a reagent component which has a bleaching action according to need. By providing such a bleaching reagent part, a so-called background, which is generated due to a color of the inspection target solution and occurs with respect to the reagent immobilization part 5 for reading a reaction, is reduced, resulting in an increase in an S/N ratio, whereby a simple and high-accuracy measurement result can be obtained. The background here is a color having no relation to the reaction, and there is a phenomenon where such color remains in the whole development layer including the reagent immobilization part in a case, for example, where the inspection target solution itself is colored. Further, the S/N ratio in this case is a ratio of a signal obtained by the marker reagent in the reaction to a so-called noise which does not derive from the marker reagent but arises from the background in a part other than the development layer.

Figure 2:
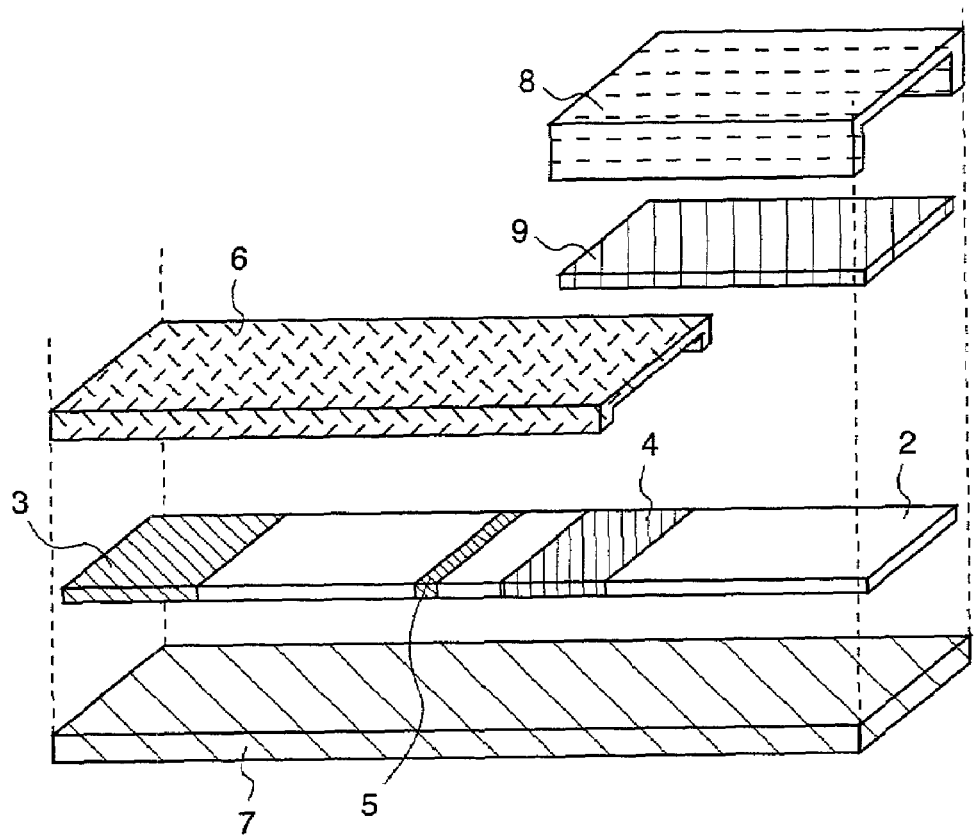
FIGS. 2(a) and 2(b) are structural diagrams of a biosensor having a separation layer according to the first embodiment of the invention.
Figure 2:
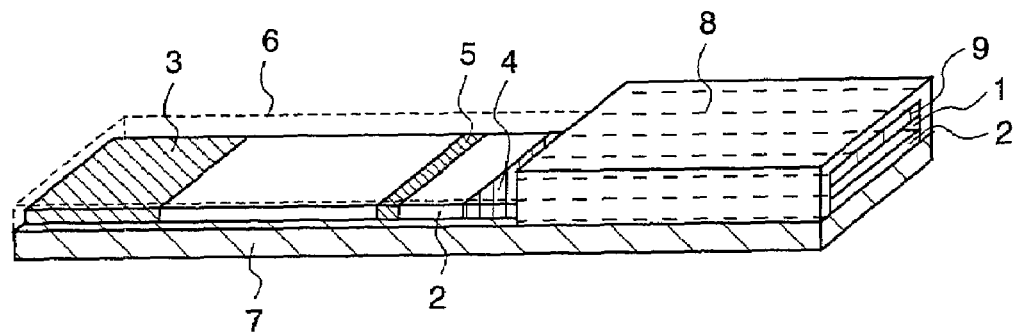

FIGS. 2(*a*) and 2(*b*) are diagrams illustrating an example of the biosensor shown in FIGS. 1(*a*) and 1(*b*), which is provided with a separation layer; where FIG. 2(*a*) is an exploded view of the biosensor and FIG. 2(*b*) is a perspective view of the biosensor. The same constitutions as those shown in FIGS. 1(*a*) and 1(*b*) are denoted by the same reference numerals, and their descriptions will be omitted.

Numeral 9 denotes a separation layer which can separate concrete components unnecessary for a measurement, and is composed of glass fiber filter paper. The glass fiber filter paper is employed as the separation layer 9 as an example, and any arbitrary materials which can be penetrated by the inspection target solution, such as a nonwoven fabric, filter paper, a glass fiber, a membrane filter, and a cloth, are available, as for the material employed for the development layer 2. Particularly, when a porous material which can be permeated is employed as the separation layer 9, impurities are trapped, thereby to prevent the impurities from flowing in the development layer and from blocking the permeation of components required for a measurement, and the separation layer 9 also functions as a subsidiary material for the inspection target solution flowing-in, whereby the inspection target solution easily flows in the cavity part 1.

Figure 3:
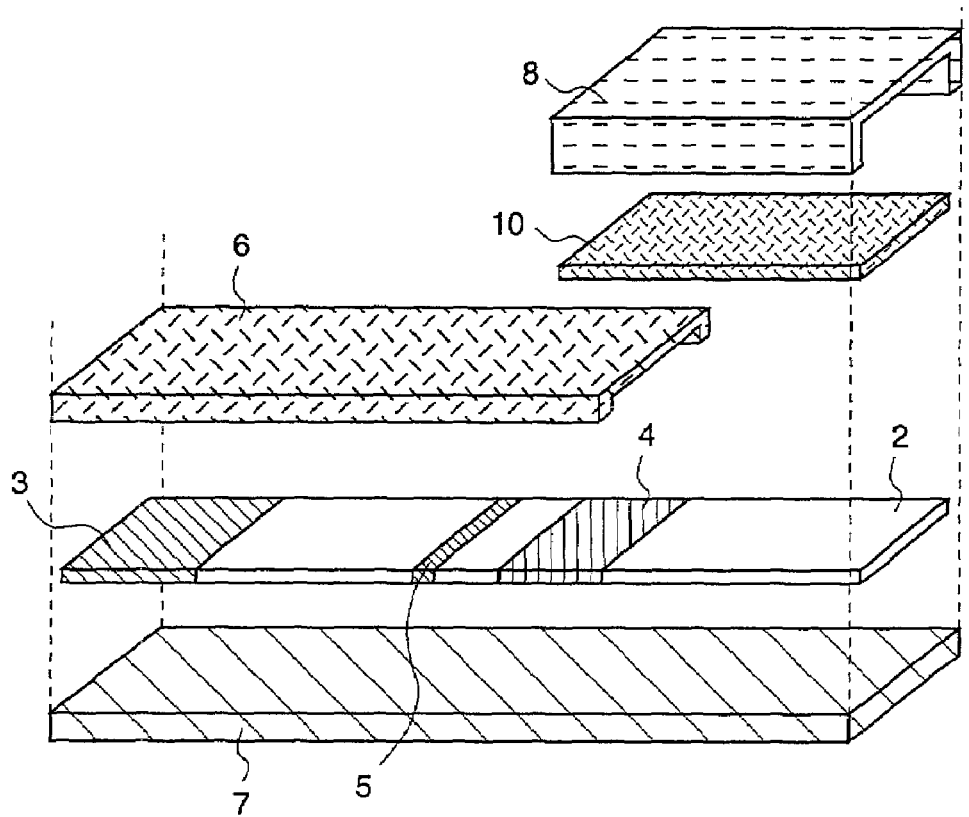
FIGS. 3(a) and 3(b) are structural diagrams of a biosensor having a cell component destruction reagent part according to the first embodiment of the invention.
Figure 3:
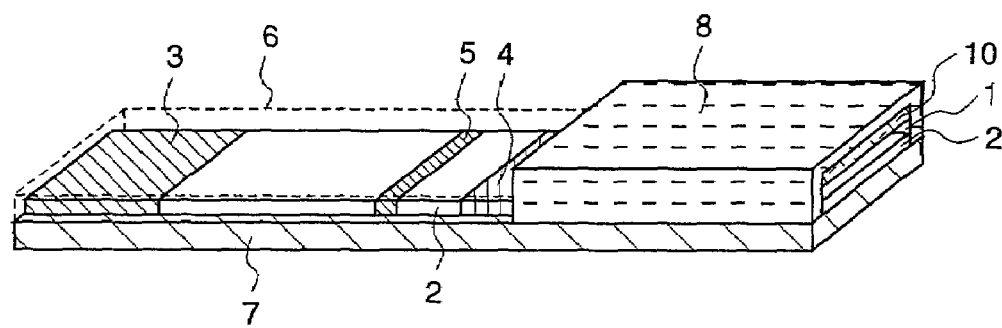

FIGS. 3(*a*) and 3(*b*) are diagrams of an example of the biosensor shown in FIG. 1, which is provided with a cell component destruction reagent part; where FIG. 3(*a*) is an exploded view of the biosensor and FIG. 3(*b*) is a perspective view of the biosensor. The same constitutions as those shown in FIGS. 1(*a*) and 1(*b*) are denoted by the same reference numerals, and their descriptions will be omitted.

Numeral 10 denotes a cell component destruction reagent part where a cell component destruction reagent for destroying cell components, and sodium chloride is dried and is held in the state where it can be eluted by the permeation of the inspection target solution. In addition to the sodium chloride, the cell component destruction reagent part 10 may be composed of an arbitrary reagent which destroys cell components, such as a surface active agent, a chloride, saponins, and lysozym.

Next, a measuring method of the biosensor according to the first embodiment of the present invention will be described with reference to FIGS. 1(*a*), 1(*b*), 2(*a*), 2(*b*), 3(*a*) and 3(*b*).

First, when the inspection target solution is brought into contact with the cavity part 1, the inspection target solution flows into the cavity part 1 by a capillary phenomenon. The inspection target solution flowing in the cavity part 1 permeates the end side of the development layer 2 from a part where the cavity part 1 is in contact with the development layer 2. When the inspection target solution reaches the marker reagent holding part 4, the marker reagent marked in the marker reagent holding part 4 starts to be eluted. At this time, when a measurement target exists in the inspection target solution, the permeation is progressed while a gold colloid marked antibody reacts from the marker reagent holding part 4. Then, when the inspection target solution reaches the reagent immobilization part 5, in a case where the measurement target exists, a complex of the immobilized antibody, the measurement target, and the marked antibody is formed according to the amount of the measurement target existing. On the other hand, when the measurement target does not exist or exists in an amount under detection sensitivity, most of the marked antibody passes on the development layer 2 without forming the complex. Then, the inspection target solution permeating on the development layer 2 is absorbed at the water absorbing layer 3, and the measurement is ended. The measurement result is obtained by confirming a bonding state of the marker reagent in the reagent immobilization part 5.

In a case where the separation layer 9 is held in the space of the cavity part 1 as shown in FIGS. 2(*a*) and 2(*b*), when the inspection target solution is brought into contact with the cavity part 1, the separation layer 9 provided in the cavity part 1 separates impurities in the inspection target solution, which are unnecessary for the measurement or separates concrete components, and the inspection target solution with its impurities and concrete components eliminated permeates the development layer 2, thereby performing a measurement.

Further, in a case where the biosensor as shown in FIGS. 3(*a*) and 3(*b*) which has the cell component destruction reagent part 10 in the space of the cavity part 1 is employed when an inspection reagent solution including cell components such as whole blood is employed, when the inspection target solution is brought into contact with the cavity part 1, the cell component destruction reagent part 10 provided in the cavity part 1 subjects the cell component such as a whole blood included in the inspection target solution to a destruction processing, and the inspection target solution with its cell components eliminated permeates the development layer 2, thereby performing a measurement.

As described above, according to the biosensor in the first embodiment, the space forming material 8 for forming space is arranged on the development layer 2 and the inspection target solution is brought into contact with the cavity part 1 which is formed by the development layer 2 and the space forming material 8, so as to perform a measurement, whereby there is no need to use a high-accuracy dispenser or the like, and, even when a small and unknown amount of inspection target solution is dropped, the drop is brought into contact with the cavity part 1, so that the inspection target solution is surely absorbed into the space, resulting in a simple and high-accuracy measurement.

Further, since the separation layer 9 is provided in the space part of the cavity part 1 according to need, unnecessary concrete components can be eliminated when the unnecessary concrete components exist or possibly exist in the inspection target solution to be measured, whereby an operation of centrifugation, filtration, or the like is not required previously, resulting in a high-accuracy measurement with a simple operation.

Further, since the cell component destruction reagent part 10 is provided on the development layer 2, a measurement employing the inspection target solution which includes cell components such as blood can be performed with whole blood as the inspection target solution directly, without requiring an operation of centrifugation or the like previously, thereby performing a simple and high-accuracy measurement.

Further, to confirm whether the amount of the inspection target solution flowing-in is enough or not or that the measurement is started, or to confirm a kind of the inspection target solution or the like, a construction which enables the confirmation through the space forming material 8 is also available. The volume of the inspection target solution flowing into the cavity part 1 is defined by the volume of the cavity part 1, thereby to perform measuring according to the amount of the collected inspection target solution. The cavity part 1 has a volume therein for the flowing-in of a sufficient amount of inspection target solution, so that specimen shortages are solved, resulting in a more accurate measurement.

Further, a visual measurement is also possible when a qualitative judgement is required. To perform an accurate measurement, side faces of the development layer 2 parallel to the direction of the inspection target solution permeating and the top surface of the development layer 2 are adherently sealed with the liquid-impermeable sheet material, so as to rectify the permeation of the inspection target solution, thereby forming a more uniform amount of complex according to the amount of the measurement target in the inspection target solution. Further, a quantitative result can also be obtained by measuring the bonding amount of a marker employing an optical method.

While in the first embodiment of the present invention the antigen antibody reaction in the sandwich reaction by which a complex of the immobilized antibody, the measurement target, and the marked antibody is formed is described, a competitive reaction is also available when a reagent which competitively reacts to the measurement target in the inspection target solution is employed according to selection of the reagent. Further, when a specific bonding is to be utilized, reactions other than the antigen antibody reaction can also be constituted by arbitrary reagent components.

Embodiment 2

Figure 4:
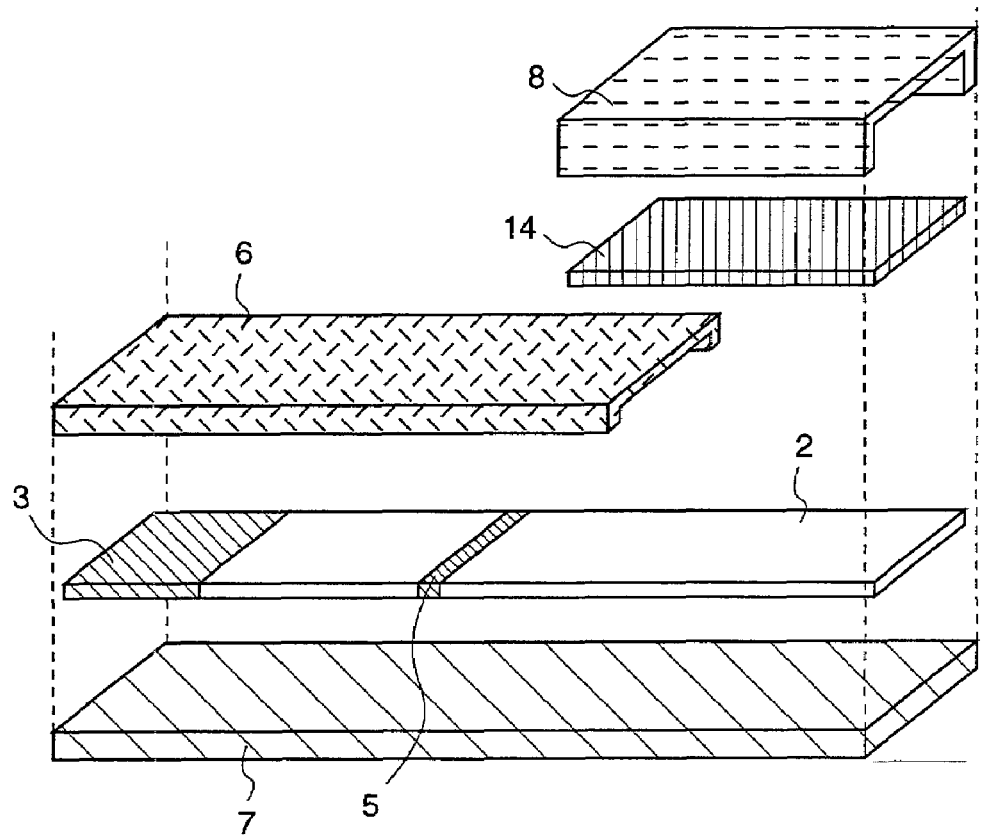
FIGS. 4(a) and 4(b) are structural diagrams of a biosensor according to a second embodiment of the present invention.
Figure 4:
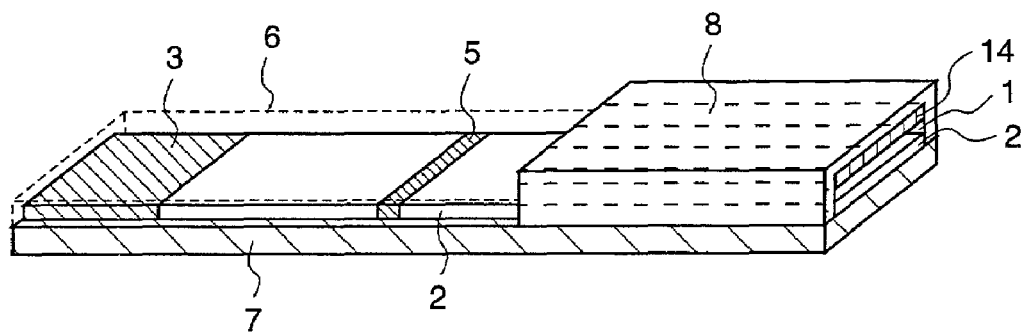

FIGS. 4(*a*) and 4(*b*) are examples of structural drawings of a biosensor according to a second embodiment of the present invention; where FIG. 4(*a*) is an exploded view of the biosensor and FIG. 4(*b*) is a perspective view of the biosensor. The same constitutions as those shown in FIGS. 1(*a*) and 1(*b*) are denoted by the same reference numerals, and their descriptions will be omitted.

The difference in constitution between FIGS. 4(*a*) and 4(*b*) and FIGS. 1(*a*) and 1(*b*) is that the marker reagent holding part 4 is marked on the development layer 2 in FIGS. 1(*a*) and 1(*b*) while a marker reagent holding layer 14 holding a marker reagent is laminated on the development layer 2 in FIGS. 4(*a*) and 4(*b*).

Next, a measuring method of the biosensor according to the second embodiment of the present invention will be described with reference to FIGS. 4(*a*) and 4(*b*).

First, when the inspection target solution is brought into contact with the cavity part 1, the inspection target solution flows into the cavity part 1 by a capillary phenomenon. The inspection target solution flowing in the cavity part 1 permeates the end side of the development layer 2 from a part where the marker reagent holding layer 14, the cavity part 1, and the development layer 2 are in contact with each other. At this time, the marked marker reagent starts to be eluted from the marker reagent holding layer 14 laminated on the development layer 2. When a measurement target exists in the inspection target solution, the permeation is progressed while a gold colloid marked antibody reacts from the marker reagent holding layer 14. Then, when the inspection target solution reaches the reagent immobilization part 5, in a case where the measurement target exists, a complex of the immobilized antibody, the measurement target, and the marked antibody is formed according the amount of the measurement target existing. On the other hand, when the measurement target does not exist or exists in an amount under detection sensitivity, most of the marked antibody passes on the development layer 2 without forming the complex. Then, the inspection target solution permeating on the development layer 2 is absorbed at the water absorbing layer 3, and the measurement is ended. The measurement result is obtained by confirming a bonding state of the marker reagent in the reagent immobilization part 5.

As described above, according to the biosensor in the second embodiment, the marker reagent holding layer 14 where the marker reagent is held is laminated on the development layer 2 and the inspection target solution is brought into contact with the cavity part 1 which is formed by the development layer 2 and the marker reagent holding layer 14, so as to perform a measurement, and therefore, the marker reagent eluted in the inspection target solution is not held in a carrier such as filter paper and is dissolved and diffused in the inspection target solution in the cavity part 1, whereby more uniform diffusion of the marker reagent with respect to the inspection target solution is possible, resulting in a more accurate biosensor.

The reagent component required for the measurement is formed in the space in a dry state as the marked antibody, thereby entirely uniformly eluting the inspection target solution required for the measurement. The reagent component required for the measurement here is a cell component destruction reagent, an enzyme substrate, an aggregation reagent, a buffering solution reagent, a protein protection reagent, or the like, and various reagent components required for the measurement can be arbitrarily introduced.

Further, the separation layer 9 is provided in the space part of the cavity part 1 according to need, unnecessary concrete components can be eliminated when the unnecessary concrete components exist or possibly exist in the inspection target solution to be measured, whereby an operation of centrifugation, filtration, or the like is not required previously, resulting in a high-accuracy measurement with a simple operation.

Further, the cell component destruction reagent part 10 is provided in the space part of the cavity part 1, whereby a measurement employing the inspection target solution which includes cell components such as blood can be preformed with whole blood as the inspection target solution directly, without requiring an operation of centrifugation or the like previously, resulting in a simple and high-accuracy measurement.

Further, to confirm whether the amount of the inspection target solution flowing-in is enough or not or that the measurement is started, or to confirm a kind of the inspection target solution or the like, a construction which enables the confirmation through the space forming material 8 is also available.

The volume of the inspection target solution flowing into the cavity part 1 is defined by the volume of the cavity part 1, thereby to perform measuring according to the amount of the collected inspection target solution.

The cavity part 1 has a volume therein for the flowing-in of a sufficient amount of inspection target solution, so that specimen shortages are solved, resulting in a more accurate measurement.

Further, a visual measurement is also possible when a qualitative judgement is required. To perform an accurate measurement, side faces of the development layer 2 parallel to the direction of the inspection target solution permeating and the top surface of the development layer 2 are adherently sealed with the liquid-impermeable material, so as to rectify the permeation of the inspection target solution, thereby forming a more uniform amount of complex according to the amount of the measurement target in the inspection target solution. Further, a quantitative result can also be obtained by measuring the bonding amount of a marker employing an optical method.

While in the second embodiment of the present invention the antigen antibody reaction in the sandwich reaction by which a complex of the immobilized antibody, the measurement target, and the marked antibody is formed is described, a competitive reaction is also available when a reagent which competitively reacts to the measurement target in the inspection target solution is employed according to selection of the reagent. Further, when a specific bonding is to be utilized, reactions other than the antigen antibody reaction can also be constituted by arbitrary reagent components.

Embodiment 3

Figure 6:
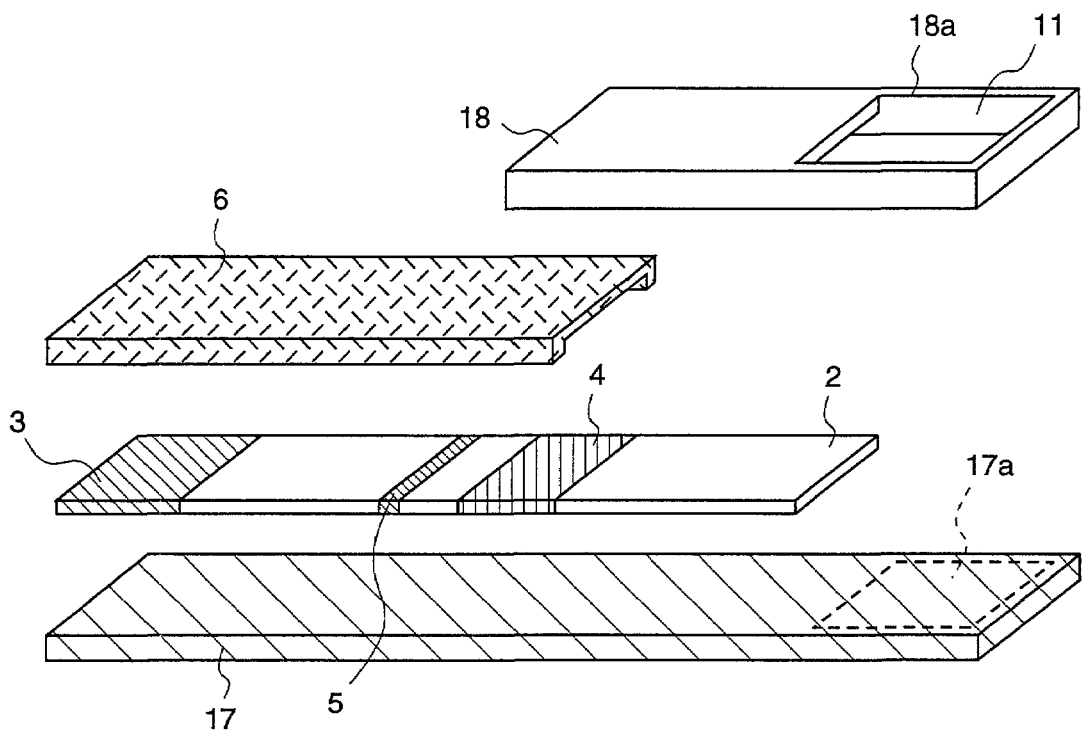
FIGS. 6(a) and 6(b) are structural diagrams of a biosensor according to a third embodiment of the present invention.
Figure 6:
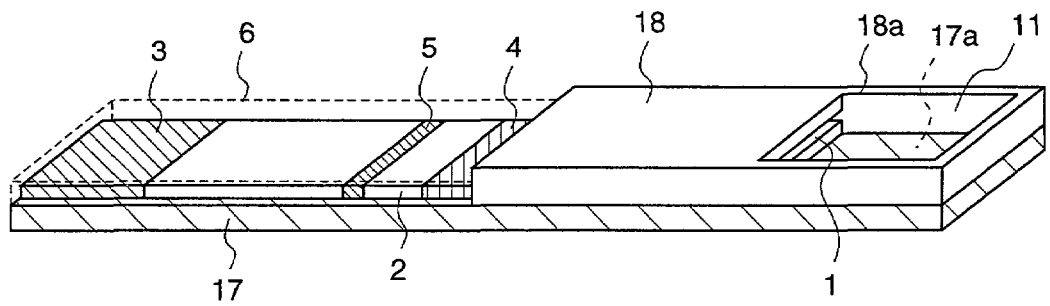

FIGS. 6(a) and 6(b) are structural drawings of a biosensor according to a third embodiment of the present invention; where FIG. 6(a) is an exploded view of the biosensor and FIG. 6(b) is a perspective view of the biosensor. In the drawings, the same reference numerals as those shown in FIGS. 1(a) and 1(b) denote the same or corresponding parts.

In FIGS. 6(a) and (b), a base material 17 holding the development layer 2 is composed of a white PET film. The base material 17 is longer than the development layer 2 in the longitudinal direction and is provided with a specimen holding region 17a as a region where the development layer 2 is not arranged in the vicinity of the end of the base material 17. This base material 17 plays a role of reinforcing the development layer 2, and when a solution which poses a risk of infection, such as blood, saliva, and urine, is employed as the inspection target solution, the base material 17 can also intercept its permeation. Further, it is also possible that the base material 17 has effects of intercepting light in a case where the permeated development layer 2 becomes light permeable. Numeral 18 denotes a space forming material for forming a cavity part 1 that is a space through which the inspection target solution flows into the development layer 2 by a capillary phenomenon, and is composed of laminated transparent PET films here. This space forming material 18 is arranged to cover the development layer 2 and the specimen holding region 17a, and ends of the space forming material 18 except for the end which faces the reagent immobilization part 5 adhere closely to the rim of the base material 17. This space forming material 18 also plays a role of protecting from pollution by the improvident inspection target solution being attached or scattering to the outside, when a biosensor to which the inspection target solution has been applied is handled. The space forming material 18 may be composed of a synthetic resin material such as ABS, polystyrene, and polyvinyl chloride, as well as a solution-impermeable material such as metal and glass, and, while the material is preferably transparent or translucent, if not transparent, a colored or opaque material is also available. An open part 18*a* is provided in the region on the specimen holding region 17*a* of the space forming material 18. This open part 18*a*, the specimen holding region 17*a*, and a part of the space forming material 18 surrounding the specimen holding region 17*a* constitute a specimen holding part 11 as a part to which the inspection target solution is applied from the outside. Numeral 1 denotes a cavity part formed by arranging the space forming material 18 on the development layer 2.

The example described in the first embodiment is suitable for a case of direct application from fingertip blood which employs small amount blood collection by a needle for small amount blood collection or the like. In the medical scene, however, syringe blood collection, vacuum blood collection by a vacuum blood collection tube, or the like is also frequently used. This third embodiment provides a biosensor which is suitable for a case of applying the inspection target solution from such a syringe or the like.

Figure 7:
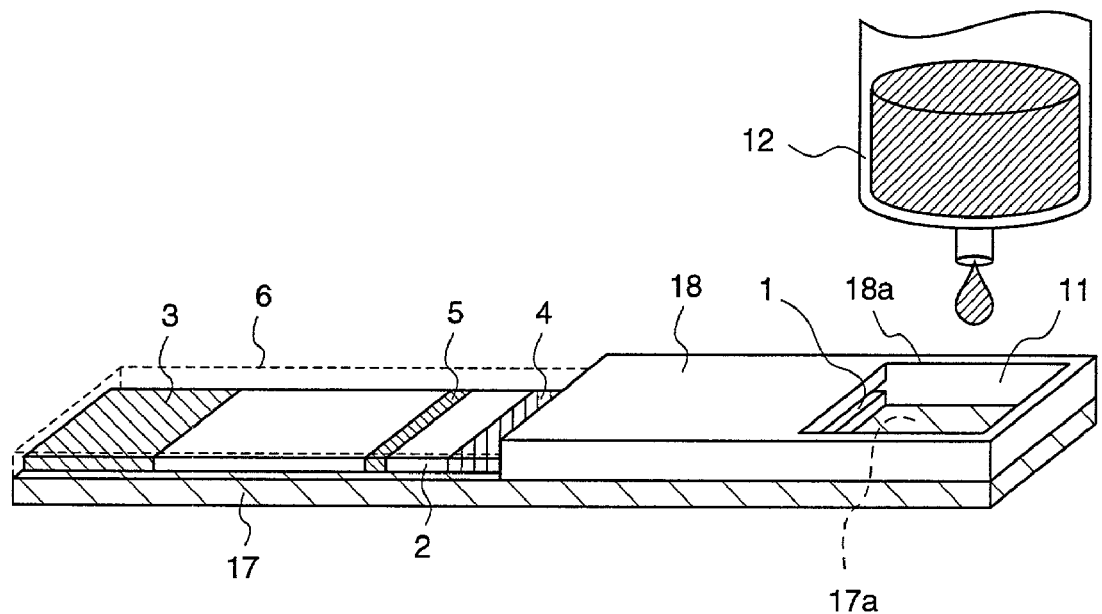
FIG. 7 is a diagram illustrating a state at a measurement employing the biosensor according to the third embodiment of the invention.

FIG. 7 is a pattern diagram illustrating a state of measurement according to the third embodiment of the present invention. In the drawing, the same reference numerals as those shown in FIG. 6 denote the same or corresponding parts, and numeral 12 denotes the vicinity of the end of a blood collection syringe after blood collection. FIG. 7 denotes a state where the inspection target solution is directly applied from the syringe 12, which has its needle part removed, after the syringe blood collection. While the needle part is removed here, it is similarly possible if the needle is kept to be connected.

In a case where the inspection target solution having cell components is taken as a specimen, a cell shrinkage reagent may be held in the cavity part 1, and potassium chloride is employed as this cell concentration reagent as an example. The cell shrinkage reagent is a reagent provided when the cell components are included in the inspection target solution, and is not particularly required when the inspection target solution including no cell components is employed. Further, the cell shrinkage reagent may be an inorganic compound including salt, such as inorganic salt other than the potassium chloride, natrium chloride, or sodium phosphate, amino acid such as glycine or glutamic acid, imino acid such as proline, sugars such as glucose, sucrose, or trehalose, and sugar alcohol such as glucitol, as long as they have effects of shrinking cells. A system including this cell component shrinker is particularly effective when whole blood is employed as the inspection target solution.

Further, sodium percarbonate can also be held as a reagent component having an bleaching action according to need. This is effective when effects of coloring matters of the inspection target solution on the measurement result cannot be neglected, for example, when a whole blood specimen is taken as the inspection target solution. While the sodium percarbonate is employed here, any reagents having a bleaching action, such as hydrogen peroxide and sodium hypochlorite, can also be selected freely in consideration of effects on the reaction.

In the constitution as described in the first embodiment which is provided only with the cavity part 1, it is likely that the inspection target solution other than that absorbed in the cavity part 1 of the biosensor is attached to the outside of the sensor to pollute the outside in the operation of directly applying the inspection target solution to the biosensor from the syringe 12. Further, in a case where the inspection target solution is not absorbed into the cavity part 1 in an amount sufficient for a measurement due to a cause that the end of the cavity part 1 is not attached to the inspection target solution perfectly or the like, an erroneous measurement result may be obtained. In such states, it is quite hard for a user to operate and there is a problem in safety and sanitation when the inspection target solution is a body fluid or the like. Further, a result lacking measurement accuracy is obtained. The safety here involves an inspector's infection by the inspection target solution and attachment thereof, or the like.

Since in the third embodiment the specimen holding part 11 for holding the specimen is provided in the vicinity of the end of the cavity part 1, a user applies the inspection target solution to the specimen holding part 11 and the inspection target solution is easily and surely held in the biosensor, thereby measuring the inspection target solution. Therefore, in a case where a measurement is implemented employing the inspection target solution which is blood collected by the so-called syringe blood collection, an operation for moving the inspection target solution to another container after the blood collection or an operation for quantitatively measuring a predetermined volume of collected inspection target solution is not required, thereby reducing outside pollution by the specimen, resulting in a safe, sanitary, quick, and simple measurement.

Further, since the inspection target solution is held in the specimen holding part 11, the inspection target solution can be held so as to be in contact with the cavity part 1, thereby absorbing the inspection target solution in a sufficient amount for an inspection into the cavity part 1.

Due to the effects of absorbing the specimen held by the cavity part 1, there is no need to quantitatively measure a predetermined amount of inspection target solution in advance, and even when an indefinite amount of inspection target solution is applied, a high-accuracy measurement is possible as in case of applying a predetermined volume of inspection target solution.

Further, the permeable material is employed for the space forming material 18 for forming the cavity part 1, thereby checking whether sufficient inspection target solution for measurement can be applied or not.

While in the third embodiment the syringe blood collection has been described, the present invention can also be applied to a measurement of the inspection target solution which employs a simple dropper, a Pasteur pipet, or the like, as well as the syringe blood collection, and further, the inspection target solution is not restricted to whole blood, and an aqueous solution, urine, saliva, blood serum, blood plasma, or the like is similarly applicable according to a purpose of a user, resulting in the same effects as in the third embodiment.

In the third embodiment, the cavity part 1 preferably has a volume of 100 μl or less. By such a construction, even in case of a measurement with a small amount of inspection target solution, such as a case where it is hard to obtain the inspection target solution or a case where the measurement is performed employing the small amount of inspection target solution, the cavity part 1 has a size enough to absorb the inspection target solution sufficiently and to ease the measurement operation, thereby enhancing the operationality of the biosensor and enabling the measurement with the small amount of inspection target solution.

Further, the specimen holding part 11 holds a larger amount of specimen than the volume of the cavity part 1, whereby the inspection target solution with sufficient volume for the measurement can be held and shortage of the inspection target solution can be solved, resulting in a highly accurate measurement. When the volume of the specimen holding part 11 is made much larger, it is possible to receive the inspection target solution in a vast amount for an amount required for a measurement, thereby preventing scattering of the inspection target solution to the outside and pollution thereby, resulting in a safer and more sanitary measurement. To allow a larger amount of inspection target solution in the specimen holding part 11 than in the cavity part as described above, the specimen holding part 11 is preferably surrounded by side walls or the like so as not to leak the inspection target solution as in the biosensor shown in FIG. 7.

While in the third embodiment the specimen holding part 11 is constituted by the base material 17 holding the development layer 2 and a part of the space forming material 18 forming the cavity part 1, it is also possible that the biosensor as described in the first embodiment is provided with a new specimen holding part which is constituted by members other than those employed for the biosensor in the present invention. Further, any constitutions which allows the specimen to be held so as to be in contact with the cavity part 1 are available as the specimen holding part.

While in the third embodiment the bottom surface of the specimen holding part 11 is the specimen holding region 17a of the base material 17 for holding the development layer 2 and the space forming material 18 provided around the specimen holding region 17a is the side wall for preventing a specimen leak, the structure which allows the inspection target solution to flow in the cavity part 1 is preferred in the present invention, and the height of the bottom surface of the specimen holding part 11 is raised with respect to the bottom surface of the cavity part 1 or the width of an application opening for applying the specimen in the specimen holding part 11 to the cavity part 1 is sufficiently narrowed and the application opening faces the cavity part 1, whereby the inspection target solution easily flows in the cavity part, resulting in a more accurate measurement.

Further, in the biosensors described in the first to third embodiments, the whole reagent including the reagent in the reagent immobilization part and the marker reagent may be in a dry state according to the present invention. Also in this case, the same effects as those in the first to third embodiments can be achieved and a biosensor which is excellent in storage stability and is freely portable can be obtained since the whole reagent is in a dry state.

Further, according to the present invention, when the same biosensor as the biosensors described in the first to third embodiments is a biosensor employed for an immuno-chromatography, in the immuno-chromatography which is prevailing in the market as a simplified method, there is no need to quantitatively measure a predetermined volume of inspection target solution with a high-accuracy dispenser or the like, and a predetermined volume of inspection target solution can be quantitatively measured accurately by the cavity part with an indefinite amount of inspection target amount being applied, thereby realizing a higher-accuracy measurement. The immuno-chromatography here is an immunoassay method by which a measurement is performed by forming a complex of the immobilized reagent and the marker reagent employing a permeable porous material, and is a system of measurement which utilizes an antigen antibody reaction and in which B/F separation is implemented in the process of the inspection target solution permeating a chromatography carrier, while a washing operation such as the B/F separation is required in a usual immunoassay method. The whole reagent is usually in a dry state and is permeated by the inspection target solution at measurement. While a gold colloid and a latex are typical as markers, magnetic particles, an enzyme, a metallic colloid, or the like are also used. When the marker is an enzyme, there is included an operation of a user adding an enzyme substrate or a reaction stop reagent as a measurement operation.

Further, according to the present invention, when the same biosensor as the biosensors described in the first to third embodiments is a biosensor employed for a one-step immuno-chromatography, in the one-step immuno-chromatography which is prevailing in the market as a simplified immunoassay method, a user does not have to quantitatively measure the volume of the inspection target solution previously, and the amount of the inspection target solution can be confirmed at measurement, thereby reducing the erroneous judgement and realizing a high-accuracy and simplified operation held by a conventional one-step immuno-chromatography. The one-step immuno-chromatography is an immunoassay method in which a measurement is started by the application of the inspection target solution employing a permeable porous material, and is a system of measurement which utilizes the antigen antibody reaction and in which the B/F separation is implemented in the process of the inspection target solution permeating a chromatography carrier, while a washing operation such as the B/F separation is required in a usual immunoassay method. The whole reagent is usually in a dry state and is permeated by the inspection target solution at measurement. This is referred to as one-step immuno-chromatography since a basic measurement operation by a user is only to apply the inspection target solution. While a gold colloid and a latex are typical as markers, magnetic particles, an enzyme, a metallic colloid, or the like are also used.

Next, the present invention will be described more specifically through examples. The present invention is not restricted to descriptions in these examples in the scope of the present invention.

Example 1

Creation of Test Strip for Measuring hCG in Urine

The immuno-chromatography development layer 2 which includes an anti-hCG-β antibody immobilization line and a broad band of a complex of an anti-hCG-α antibody and gold colloid in a nitrocellulose film was manufactured. The cavity part 1 was formed by the space forming material 8 in a part where the inspection target solution is applied on this immuno-chromatography development layer 2, thereby manufacturing an immuno-chromatography test strip. This test strip has the structure as shown in FIGS. 1(a) and 1(b). According to FIGS. 1(a) and 1(b), the test strip includes the antibody immobilization part 5 and the marker reagent holding part 4 located on the side of contacting place of the inspection target solution with respect to the antibody immobilization part, which includes the complex of the anti-hCG-α antibody and the gold colloid. These test strips were manufactured as follows.

a) Preparation of Immuno-Chromatography Development Layer

First, the anti-hCG-β antibody solution which was diluted with a phosphate buffer solution to control the concentration was prepared. This antibody solution was applied on the nitrocellulose film by employing a solution discharge device. Thereby, a detecting antibody immobilization line was obtained on the nitrocellulose film. After being dried, this nitrocellulose film was immersed in a Tris-HCl buffer solution including a 1% skim milk, and gently shaken for 30 minutes. 30 minutes later, the film was moved into a Tris-HCl buffer solution tank, gently shaken for 10 minutes, and thereafter gently shaken in another Tris-HCl buffer solution tank for another 10 minutes, thereby washing the film. After being washed twice, the film was taken out from the cleaning fluid and dried at room temperature.

The gold colloid was prepared by adding 1% citric acid solution to a refluxing 100° C.-solution of 0.01% chloroauric acid. After the reflux was continued for 30 minutes, the gold colloid was cooled and prepared to pH9 by using a 0.2M potassium carbonate solution. The anti-hCG-α antibody was added to this gold colloid solution, then the obtained solution was stirred for several minutes, and thereafter a 10% BSA (bovine serum albumin) solution pH9 was added thereto by such an amount that a 1% solution was finally obtained, and stirred. Thereby, an antibody-gold colloid complex (marked antibody) was prepared. Thereafter, the marked antibody solution was centrifuged at 4° C. and 20000 G for 50 minutes, whereby the marked antibody was isolated, and the isolated marked antibody was suspended in a cleaning buffer solution (1% BSA·phosphate buffer solution) and thereafter centrifuged to wash and isolate the marked antibody. This marked antibody was suspended in the cleaning buffer solution and filtrated through a 0.8 μm filter, thereby preparing the marked antibody to be one-tenth as much as the initial gold colloid solution and stored at 4° C.

The so-prepared marked antibody solution was set in the solution discharge device and applied to a position apart from the antibody immobilization position on the anti-hCG-β antibody immobilization dry film, and thereafter the film was dried. Thereby, the marker reagent holding region was obtained on the immobilization film. In this way, an immuno-chromatography reactive layer, that is, development layer was completed.

b) Creation of Immuno-Chromatography Test Strip The immuno-chromatography test strip was attached onto the base material made of white PET with 0.5 mm thickness and this was cut with the width of 2.5 mm. After the cutting, each piece of the immuno-chromatography was wound around with transparent tape with 100 μm thickness from the marked antibody holding part to the end of the immuno-chromatography. The space forming material having an air vent in advance which was created by laminating transparent PET with 100 μm thickness was attached to the middle on the beginning part which was not wound around with the transparent tape, thereby forming the cavity part (width 2.0 mm×length 6.0 mm·height 0.5 mm). The immuno-chromatography test strip was manufactured in this way.

c) Preparation of Sample

The hCG solutions of known concentrations were added to human urine, thereby preparing the hCG solutions of various known concentrations.

d) Measurement

Urine including the hCG with its concentration controlled was dropped on the PET base material to form a drop thereon. The formed drop was brought into contact with the cavity part of the immuno-chromatography test strip and introduced therein. The introduced drop was developed in the direction of the water absorbing layer to cause the antigen antibody reaction, thereby causing a color reaction in the antibody immobilization part. A coloration state after 5 minutes have passed since the sample application to this test strip is measured employing a reflective spectrophotometer (CS9300; manufactured by Shimadzu Corporation), and the coloration degree is computed.

First, urine including each hCG of 100, 1000, and 10000U/1 of hCG concentration were applied to the immuno-chromatography test strip to be developed. Then, the coloration state of the antibody immobilization part on the test strip for urine of each hCG concentration was measured by the reflective spectrophotometer. An absorbance at the wavelength of 520 nm was measured by the reflective spectrophotometer, and substituted into a previously formed calibration curve indicating a relationship between the hCG concentration and the absorbance. The result is shown in FIG. 5.

Figure 5:
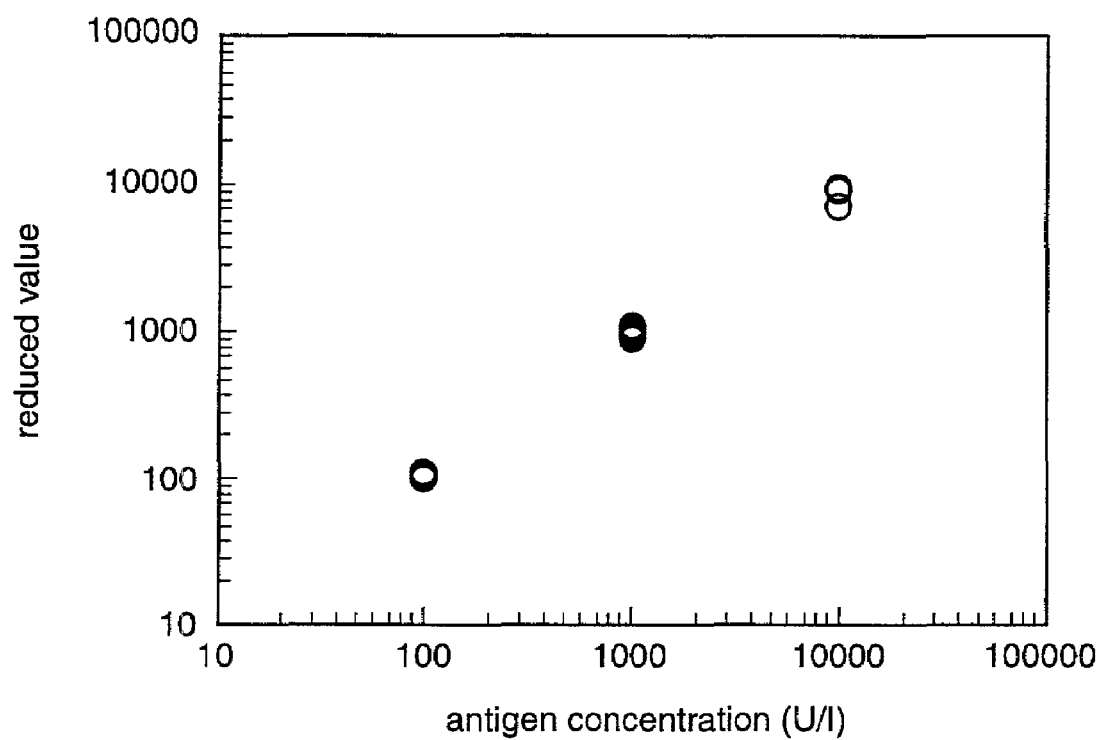
FIG. 5 is a graph illustrating a relationship between hCG concentration and an absorbance according to a first example of the present invention.

FIG. 5 illustrates the result of reducing concentration of an analysis target on the basis of a measurement value of the coloration degree after 5 minutes have passed since the start of the application, when a liquid sample is applied to the immuno-chromatography test strip. The measurement is performed at each concentration n=10, resulting in excellent correlation with CV values of 5-10%.

Example 2

Creation of Test Strip for Quantitatively Measuring Whole Blood CRP

The immuno-chromatography test strip which includes the reagent immobilization part where an anti-CRP antibody A is immobilized and the marker reagent holding a complex of an anti-CRP antibody B and gold colloid in a nitrocellulose film was manufactured. This immuno-chromatography test strip has the same constitution as the biosensor shown in FIGS. 6(a) and 6(b), and includes the marker reagent 4 as a region where the complex of the anti-CRP antibody B and gold colloid is included, which is located at a part nearer to the development start point where the inspection target solution is applied than the reagent immobilization part 5 where the antibody is immobilized is, and the specimen holding part 11. This immuno-chromatography test strip was manufactured as follows.

a) Preparation of Immuno-Chromatography Test Strip

The anti-CRP antibody A solution which was diluted with a phosphate buffer solution to control the concentration was prepared. This antibody solution was applied to the nitrocellulose film by employing a solution discharge device. Thereby, an antibody immobilization line as the reagent immobilization part was obtained on the nitrocellulose film. After being dried, this nitrocellulose film was immersed in a Tris-HCl buffer solution including a 1% skim milk, and gently shaken for 30 minutes. 30 minutes later, the film was moved into a Tris-HCl buffer solution tank, gently shaken for 10 minutes, and thereafter gently shaken in another Tris-HCl buffer solution tank for another 10 minutes, thereby washing the film. After being washed twice, the film was taken out from the fluid tank and dried at room temperature.

The gold colloid was prepared by adding 1% citric acid solution to a refluxing 100° C.-solution of 0.01% chloroauric acid. After the reflux was continued for 30 minutes, it was left and cooled at room temperature. The anti-CRP antibody B was added to the gold colloid solution which was prepared to pH9 by using a 0.2M potassium carbonate solution, then the obtained solution was stirred for several minutes, and thereafter a 10% BSA (bovine serum albumin) solution of pH9 was added thereto by such an amount that a 1% solution was finally obtained, and stirred. Thereby, an antibody-gold colloid complex (marked antibody) as a detection substance was prepared. The marked antibody solution was centrifuged at 4° C. and 20000 G for 50 minutes, whereby the marked antibody was isolated, and the isolated marked antibody was suspended in a cleaning buffer solution (1% BSA·phosphate buffer solution) and thereafter centrifuged to wash and isolate the marked antibody. After being suspended in the cleaning buffer solution and filtrated through a 0.8 μm filter, the marked antibody was prepared to be one-tenth as much as the initial gold colloid solution and stored at 4° C.

The gold colloid marked antibody solution was set in the solution discharge device and applied to a position apart from the immobilization line on the anti-CRP antibody immobilization A dry film so as to sequentially locate the marked antibody and the immobilization line from the direction of the inspection target solution application start, and thereafter the film was dried. Thereby, the reactive layer carrier including the marker reagent was obtained on the immobilization film.

Next, the prepared reactive layer carrier including the marker reagent was attached onto the base material made of white PET with 0.5 mm thickness and this was cut with the width of 5.0 mm. After the cutting, each piece was wound around with transparent tape with 100 μm thickness from the marked antibody holding part to the end of the immunochromatography. The space forming material having an air vent in advance which was created by laminating transparent PET with 100 μm thickness was attached to the middle on the beginning part which was not wound around with the transparent tape, thereby forming the cavity part (width 5.0 mm×length 12.0 mm×height 0.5 mm). Solution-leak preventing walls of the specimen holding part is previously formed in the space forming material. Further, the space forming material is created to have a shrinker holding part, in which 2 μl of potassium chloride solution previously prepared to 1.5M is applied per unit area, immediately froze by liquid nitrogen, and freeze-dried, thereby holding the potassium chloride in a dry state. The immuno-chromatography test strip was manufactured in this way.

b) Preparation of Sample

Human blood to which EDTA-2K is added as an anticoagulant is prepared to have a hematocrit value of 45%. The CRP solutions of known concentrations were added to this human blood, thereby preparing the blood including the CRP of various known concentrations.

c) Measurement of coloration degree on test strip

Considering the actual blood collection state, a syringe for 20 ml volume is filled up with the prepared whole blood and an appropriate amount of whole blood including CRP was added to the specimen holding part without measuring for a predetermined volume. After the application, the inspection target solution was absorbed in the cavity part. The inspection target solution was developed in the direction of the water absorbing part to cause the antigen antibody reaction, thereby causing a color reaction in the antibody immobilization part. A coloration state after 5 minutes have passed since the sample application to this biosensor is measured by a reflective spectrophotometer.

Figure 8:
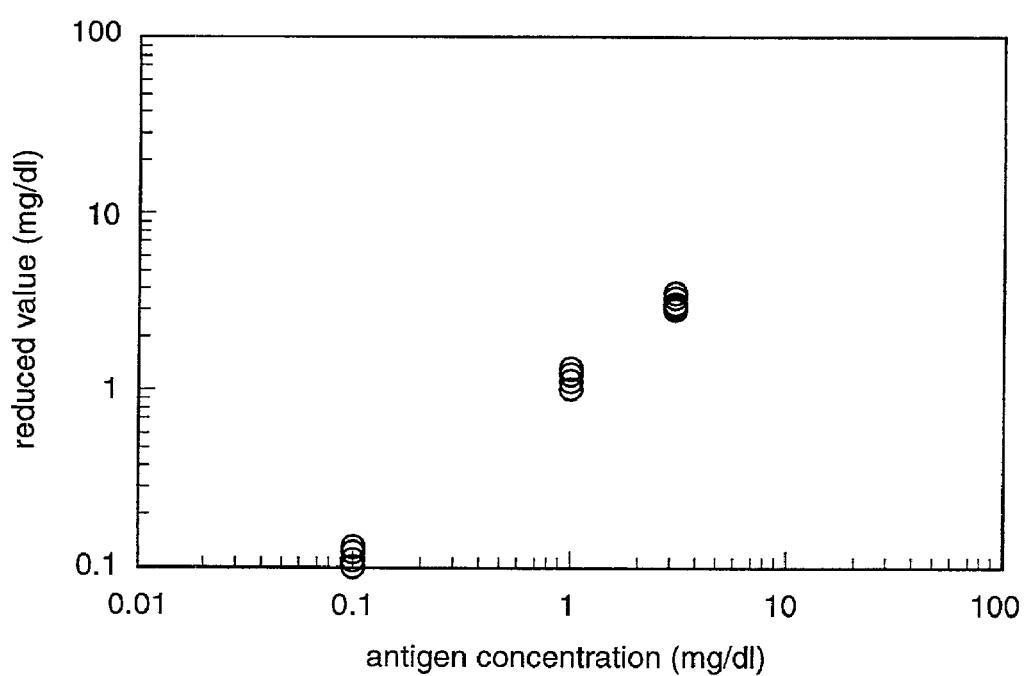
FIG. 8 is a graph illustrating a relationship between CRP concentration and an absorbance according to a second example of the present invention.

Appropriate amounts of whole blood including CRP of 0.1 mg/dl, 1.0 mg/dl, and 3.0 mg/dl of plasma concentration were directly applied to the biosensor from the 20 ml-syringe to be developed. Then, the coloration state of the reagent immobilization part on the biosensor for blood of each hCG concentration was measured by a reflective absorbance measuring device (CS-9300; manufactured by SHIMADZU). An absorbance at 635 nm was measured and plotted according to each CRP concentration. This is shown in FIG. 8. FIG. 8 is a diagram illustrating the measurement result at multiple concentrations in the second example, in which the abscissas represents the CRP concentration measured employing a commercial measuring device. Here, a reagent through a latex immuno-agglutination method is employed as the commercial measuring device. Further, the ordinate represents the obtained absorbance. A calibration curve is an area in which the absorbance increases with an increase of the CRP concentration, which is a mathematical expression usually calculated previously through the inspection target solution of known concentration, so as to calculate the CRP concentration in unknown inspection target solution thereafter from the absorbance obtained when the unknown inspection target solution is measured. As shown in FIG. 8, a preferable result was obtained as in the first example.

As a bio-device in the second example, a biosensor made of a chromatography material composed of an arbitrary porous carrier such as nitrocellulose or glass fiber filter paper is employed. The biosensor made of such a material has a function of analytically detecting and qualitatively or quantitatively measuring certain substances employing an arbitrary measurement principle such as the antigen antibody reaction.

While in the second example a biosensor in which the marker reagent and the reagent immobilization part are provided in the same nitrocellulose film is employed, it is also possible that a marker reagent in which a marker reagent is supported on a porous carrier made of a material other than the nitrocellulose, such as a nonwoven fabric, is arranged on a support body. While the gold colloid is exemplified as a marker constituting the marker reagent, anything that generates some changes before and after reaction, such as coloring substance, fluorescence substance, phosphorescence substance, luminescence substance, oxidation-reduction substance, an enzyme, a nucleic acid, and an endoplasmic reticulum, is also available.

As the inspection target solution to be measured, there are water, an aqueous solution, a body fluid such as urine, blood, blood plasma, blood serum, and saliva, a solution in which a solid, fine particles, or gas is dissolved, or the like, and their applications are for urinalysis, a pregnancy test, a water examination, an examination of the feces, soil analysis, food analysis, and the like. While the example has been described with the C-reactive protein (CRP) as the inspection target substance, an antibody, immunoglobulin, hormone, a protein and protein derivatives such as an enzyme and peptide, a bacteria, a virus, Eumycetes, mycoplasma, a parasite and infectious substance such as products and components thereof, chemicals such as curative medicine and abuse medicine, and a tumor marker are available. Specifically, for example, chrionic gonadotropin (hCG), corpus luteum hormone (LH), thyroid stimulating hormone, follicular forming hormone, parathyroid stimulating hormone, adrenal lipid stimulating hormone, estradiol, prostate specific antigen, hepatitis B surface antigen, myoglobin, CRP, myocardial troponin, HbAlc, albumin, or the like are available. Further, environmental analysis such as a water examination and soil analysis, food analysis, or the like can be also implemented. According to the embodiments, a simple, quick, highly sensitive, efficient, and accurate measurement can be realized.

APPLICABILITY IN INDUSTRY

As described above, a biosensor according to the present invention is available as a biosensor utilized for an immunochromatography or a so-called one-step chromatography, and specifically, as a biosensor utilized for a measurement in such a state where simplification or speeding-up of the operation is required as in the medical and diagnostic scene or household, or as a biosensor utilized for a measurement of small volume of inspection target solution.

The invention claimed is:

1. A biosensor comprising:
   a development layer for developing an inspection target solution as a specimen by making the inspection target solution permeate inwards, wherein said development layer includes a reagent immobilization part immobilized therein and a marker reagent holding part where a marker reagent which can be eluted by the development of the inspection target solution is held, wherein said biosensor measures a bonding amount of the marker reagent in said reagent immobilization part, thereby qualitatively or quantitatively measuring components to be measured in the inspection target solution, and wherein said biosensor further comprises:

a space forming part which forms a cavity part, wherein said cavity part is a space into which the inspection target solution flows by a capillary phenomenon, wherein said space forming part is located only at a part upstream of said reagent immobilization part in a permeating direction of the inspection target solution, wherein an amount of inspection target solution which flows into said cavity part is regulated by a volume of said cavity part, and wherein, by permeating the inspection target solution of the amount regulated by the volume of said cavity part into said development layer, B/F separation of the marker reagent in said reagent immobilization part is implemented.

2. The biosensor as defined in claim 1, wherein
said cavity part temporarily holds the inspection target solution.

3. The biosensor as defined in claim 1, further including
a cell component destruction reagent part for destroying cell components in said cavity part.

4. The biosensor as defined in claim 1, further including
a cell component shrinkage reagent part for shrinking cell components in said cavity part.

5. The biosensor as defined in claim 1, further including
a bleaching reagent part in said cavity part.

6. The biosensor as defined in claim 1, wherein
said cavity part has a volume of 20 µl or less.

7. The biosensor as defined in claim 1, wherein
said cavity part has a means for externally checking whether the inspection target solution flowed inwards or not.

8. The biosensor as defined in claim 1, wherein
said space forming part is partially or entirely light permeable.

9. The biosensor as defined in claim 1, further including a separation part for separating concrete components unnecessary for a measurement in said cavity part.

10. The biosensor as defined in claim 1, wherein
said space forming part includes an air vent for assisting the inspection target solution in flowing into said cavity part.

11. The biosensor as defined in claim 1, further including
a porous material which can be permeated by permeation of the inspection target solution in said cavity part.

12. The biosensor as defined in claim 1, wherein
the reagent in said reagent immobilization part and the marker reagent are in a dry state.

13. The biosensor as defined in claim 1, wherein
the biosensor is employed for an immuno-chromatography.

14. The biosensor as defined in claim 1, wherein
the biosensor is employed for a one-step immuno-chromatography.

15. The biosensor as defined in claim 1, wherein a portion of said development layer, other than a portion of said development layer facing said cavity party, is adherently covered by a liquid-impermeable material.

16. The biosensor as defined in claim 1, wherein said development layer is disposed so that only a portion of said development layer is able to contact an externally located inspection target solution, the portion of said development layer which is able to contact the externally located inspection target solution facing said cavity part.

17. A biosensor comprising: a development layer for developing an inspection target solution as a specimen by making the inspection target solution permeate inwards; and a reagent immobilization part immobilized in a part of said development layer for developing the inspection target solution, wherein said biosensor measures a bonding amount of the marker reagent in the reagent immobilization part, thereby qualitatively or quantitatively measuring components to be measured in the inspection target solution, and wherein said biosensor further comprises:

a space forming part which forms a cavity part, wherein said cavity part is a space into which the inspection target solution flows by a capillary phenomenon; and a marker reagent holding part for holding a marker reagent which can be eluted by flowing-in of the inspection target solution, in said cavity part, wherein said space forming part is located only at a part upstream of said reagent immobilization part in a permeating direction of the inspection target solution, wherein an amount of inspection target solution which flows into said cavity part is regulated by a volume of said cavity part, and wherein, by permeating the inspection target solution of the amount regulated by the volume of said cavity part into said development layer, B/F separation of the marker reagent in said reagent immobilization part is implemented.

18. The biosensor as defined in claim 17, wherein
said cavity part temporarily holds the inspection target solution.

19. The biosensor as defined in claim 17, further including
a cell component destruction reagent part for destroying cell components in said cavity part.

20. The biosensor as defined in claim 17, further including
a cell component shrinkage reagent part for shrinking cell components in said cavity part.

21. The biosensor as defined in claim 17, further including
a bleaching reagent part in said cavity part.

22. The biosensor as defined in claim 17, wherein
said cavity part has a volume of 20 µl or less.

23. The biosensor as defined in claim 17, wherein
said cavity part has a means for externally checking whether the inspection target solution flowed inwards or not.

24. The biosensor as defined in claim 17, wherein
said space forming part is partially or entirely light permeable.

25. The biosensor as defined in claim 17, further including
a separation part for separating concrete components unnecessary for a measurement in said cavity part.

26. The biosensor as defined in claim 17, wherein
said space forming part includes an air vent for assisting the inspection target solution in flowing into said cavity part.

27. The biosensor as defined in claim 17, further including
a porous material which can be permeated by permeation of the inspection target solution in said cavity part.

28. The biosensor as defined in claim 17, wherein
the reagent in said reagent immobilization part and the marker reagent are in a dry state.

29. The biosensor as defined in claim 17, wherein the biosensor is employed for an immuno-chromatography.

30. The biosensor as defined in claim 17, wherein the biosensor is employed for a one-step immuno-chromatography.

31. The biosensor as defined in claim 17, wherein a portion of said development layer, other than a portion of said development layer facing said cavity party, is adherently covered by a liquid-impermeable material.

32. The biosensor as defined in claim 17 wherein said development layer is disposed so that only a portion of said development layer is able to contact an externally located inspection target solution, the portion of said development layer which is able to contact the externally located inspection target solution facing said cavity part.

* * * * *

UNITED STATES PATENT AND TRADEMARK OFFICE
CERTIFICATE OF CORRECTION

PATENT NO. : 7,575,915 B2  
APPLICATION NO. : 10/031988  
DATED : August 18, 2009  
INVENTOR(S) : Masataka Nadaoka et al.

Page 1 of 1

It is certified that error appears in the above-identified patent and that said Letters Patent is hereby corrected as shown below:

On the Title Page

Please insert the following:

--(30)  Foreign Application Priority Data

May 26, 2000      [JP]    Japan......................2000-157049--

Signed and Sealed this  
Sixth Day of May, 2014

Michelle K. Lee  
*Deputy Director of the United States Patent and Trademark Office*